United States Patent [19]

Chiba et al.

[11] Patent Number: 5,142,079
[45] Date of Patent: Aug. 25, 1992

[54] FLUORINATED CARBON CHAIN-CONTAINING ALUMINUM SURFACE MODIFIER

[75] Inventors: Naoki Chiba; Koichiro Sagawa, both of Kawasaki, Japan

[73] Assignee: Ajinomoto Co., Inc., Tokyo, Japan

[21] Appl. No.: 625,490

[22] Filed: Dec. 11, 1990

[30] Foreign Application Priority Data

Dec. 11, 1989 [JP] Japan ................... 1-321038

[51] Int. Cl.$^5$ ............................. C07F 5/06
[52] U.S. Cl. ........................ 556/183; 556/27; 556/174; 556/177; 106/241; 106/266; 106/400; 106/401
[58] Field of Search .............. 556/27, 183, 174, 177; 106/241, 266, 400, 401

[56] References Cited

U.S. PATENT DOCUMENTS 3,465,014 2/1969 Pavlik ........................... 260/448
4,576,647 3/1986 Matsushita .................. 106/193 R

FOREIGN PATENT DOCUMENTS 0212820 4/1987 European Pat. Off. .
0340753 8/1989 European Pat. Off. .

Primary Examiner—Jose G. Dees
Assistant Examiner—Porfirio Nazario
Attorney, Agent, or Firm—Oblon, Spivak, McClelland, Maier & Neustadt

[57] ABSTRACT

The novel fluorinated carbon chain-containing aluminum compounds which are capable of imparting an SP value of desired level to inorganic materials and hence can be used as surface modifiers for improving the affinity between inorganic materials and fluororesins, fluorine-containing paints are disclosed.

4 Claims, 10 Drawing Sheets

FLUORINATED CARBON CHAIN-CONTAINING ALUMINUM SURFACE MODIFIER

BACKGROUND OF THE INVENTION

1. Field of the Invention

The present invention relates to a surface modifier for imparting properties characteristic of fluorocarbons to the surface of inorganic materials.

2. Discussion of the Background

Among known fluorine-containing surfactants or surface modifiers are fluorine-containing compounds, including those which contain a hydrophobic group of a long fluorocarbon chain and a hydrophilic group, such as $-SO_3H$ and $-CO_2H$, or, in place of such a hydrophilic group, a hydrocarbon chain. Such fluorine-containing surfactants or surface modifiers (1) are capable of lowering the surface tension of water to a considerable degree, (2) exhibit a high surface activity at a low concentration, (3) are excellent in heat and chemical resistance, (4) can exhibit surface activities in organic solvents and (5) possess both water and oil repellency, and hence they can be superior to prior hydrocarbon surfactants or surface modifiers. However, they are poor in their bonding power to the surface of inorganic materials. It is also known that hydrocarbon chain-containing aluminum compounds can be useful as surface modifiers since the compounds can be bonded, by means of a covalent bond, to the surface of inorganic materials, thus imparting thereto such properties as water and oil repellency. It is, however, difficult to disperse fillers treated with such a fluorinated carbon chain-containing aluminum compound into a fluororesin or to use such a compound as a primer for fluorine-containing paints. The reason for this can be attributed to the fact that the SP values of fluororesins and fluorine-containing paints are low. Although fluororesins have excellent properties characteristic of fluorine compounds, such as excellent chemical resistance, heat resistance and electrical properties, the resins suffer from the disadvantages that their price is high, and they are poor in molding property, coloring property and processability upon filling of inorganic fillers. Fluorine-containing paints are disadvantageous in that they are poor in coloring property, which is basic for paints. Because of their low surface energy, fluorine-containing paints are also poor in adhesive powder to materials to be painted and hence require the use of an excellent primer.

Japanese Patent Applications (Laid Open) Nos. 254,119/85 and 297,478/86 describe fluorinated carbon chain-containing couplers, in particular, titanate couplers. However, it is also known that aluminate couplers are more effective than such titanate couplers, as far as effects for certain kinds of fillers, such as carbon black or the like.

SUMMARY OF THE INVENTION

It is a primary object of the present invention to provide novel fluorinated carbon chain-containing aluminum compounds which are capable of imparting an SP value of the desired level to inorganic materials and hence can be used as a surface modifier for improving the affinity between inorganic materials and fluororesins, fluorine-containing paints, or the like.

It in an object of the present invention to provide a surface modifier which is capable of strongly adhering to the surface of an inorganic material.

It is another object of the present invention to provide surface modifier capable of imparting an SP value of desired level to the surface of an inorganic material, so as to make it possible to fill the material into a fluororesin to be improved.

It is a further object of the present invention to provide a surface modifier which can be used as an effective primer upon the coating of a fluorine-containing paint or upon the formation of a fluororesin film.

BRIEF DESCRIPTION OF THE DRAWINGS

FIG. 1: Isopropoxynonadecafluoodecanoylaluminum ethylacetoacetate

FIG. 2: Isopropoxynonadecafluorodecanoylaluminum octylacetoacetate

FIG. 3: Aluminum triisopropoxide

FIG. 6: Nonadecafluorodecanoic acid.

FIG. 7: Isopropoxy 1H,1H,2H,2H-perfluorodecanoxyaluminum ethylacetoacetate

FIG. 8: Isopropoxy 1H,1H,2H,2H-perfluorodecanoxyaluminum octadecylacetoacetate

FIG. 9: Isopropoxy 1H,1H,2H,2H-perfluorodecanoxyaluminum acetylacetonate

FIG. 10: Diisopropoxyaluminum 1H,1H,2H,2H-perfluorodecyl acatoacetate

FIG. 11: Isopropoxy di-1H,1H,2H,2H-Perflyorodecanoxyaluminum

FIG. 12: Acetylacetone

FIG. 13; 1H,1H,2H,2H-perfluorodeoanol

DETAILED DESCRIPTION OF THE PREFERRED EMBODIMENTS

Figure 1:
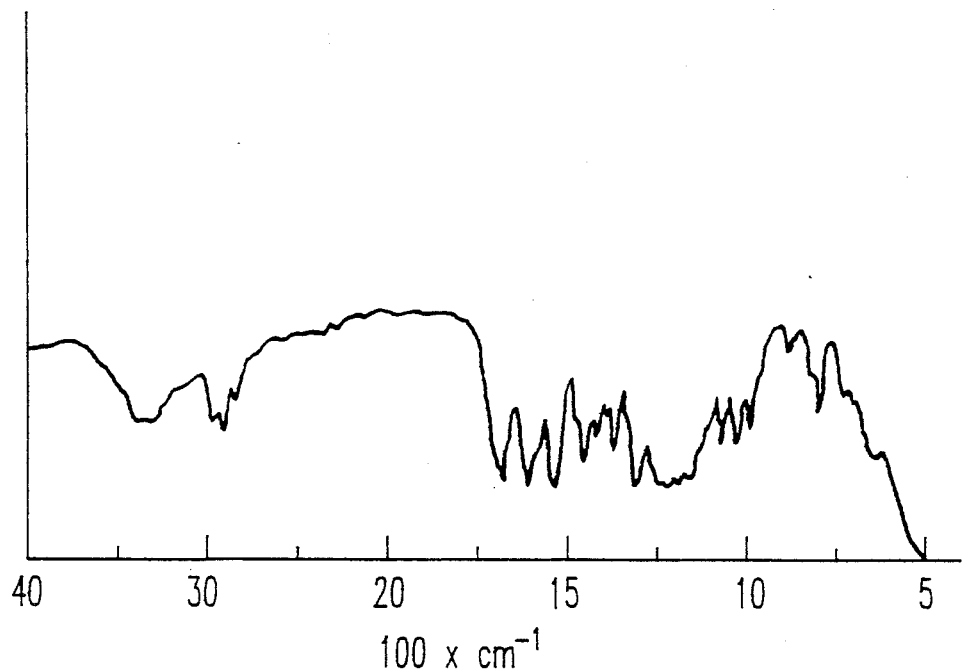
FIGS. 1, 2, 7, 8, 9, 10 and 11 show infrared absorption spectra of products according to the invention.

It has now been found that a certain fluorinated carbon chain-containing aluminum compounds are capable of imparting an SP value of desired level to inorganic materials and hence can be used as a surface modifier for improving the affinity between inorganic materials and fluororesins, fluorine-containing paints, or the like. The present invention has been completed on the basis of the above finding:

Accordingly, the present invention is concerned with a fluorine-containing surface modifier comprising at least one member selected from the group consisting of: (1) fluorinated carbon chain-containing aluminum compounds represented by General Formula (1), (2) or (3) of the following:

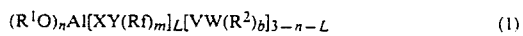

-continued

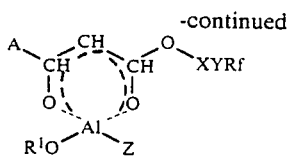
(3)

wherein n, m, L and b represent an integer of 1 or 2 (n and L satisfy: n+L<3); X and V represent

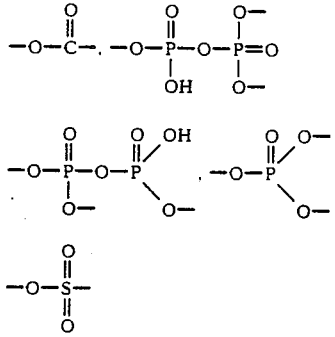

or $-O-$; Y and W represent $-C_kH_{2k}-$, $-(C_kH_{2k}O)_g-$ or a covalent bond (in which k represents an integer of 1 to 30, and g represents an integer of 1 to 10); $R^1$ and $R^2$ represents an alkyl group containing 1 to 30 carbon atoms; Rf represents $C_qF_{2q+1}$ or $C_qF_{2l}H$; A and B represent $C_pH_{2p+1}$ or $C_JH_{2J+1}O$ (in which p, q and J represent an integer of 1 to 30); and Z represents $VR^2$ or VWRF); and (2) fluorinated carbon chain-containing aluminum compounds obtainable by:

alkoxy exchange reaction of an alkoxy aluminum compound selected from of Group I (general formula 4) set forth below with a fluorinated carbon chain-containing compound represented by General Formula (7) set forth below and a hydrocarbon chain-containing compound represented by General Formula (8) set forth below, in which said fluorinated carbon chain-containing compound is used in an amount of x mol and said hydrocarbon chain-containing compound in an amount of y mol, per mol of said alkoxy aluminum compound, wherein x and y are numerals that satisfy:

$0.1 \leq x \leq 2.5$, $0.1 \leq y \leq 2.5$ and $0.1 \leq x+y \leq 2.5$;

alkoxy exchange reaction of an alkoxy aluminum compound selected from Group I set forth below with a dicarbonyl compound represented by General Formula (5) set forth below and a fluorinated carbon chain-containing compound represented by General Formula (7) sat forth below, in which said fluorinated carbon chain-containing compound is used in an amount of x mol and said hydrocarbon chain-containing compound in an amount of y mol, per mol of said alkoxy aluminum compound (wherein x and y are numerals that satisfy: $0.1 \leq x \leq 2.5$, $0 \leq y \leq 2.5$ and $x+y \leq 2.5$); or alkoxy exchange reaction of an alkoxy aluminum compound selected from Group I set forth below with a dicarbonyl compound represented by General Formula (6) set forth below and a compound represented by General Formula (7) or (8) of Group III set forth below, in which said dicarbonyl compound is used in an amount of x mol and said Group III compound in an amount of y mol, per mol of said alkoxy aluminum compound (wherein x an y are numerals that satisfy: $0.1 \leq x \leq 2.5$, $0 \leq y \leq 2.5$ and $0.1 \leq x+y \leq 2.5$).

Group I: $(R^1O)_3Al$ (4)

Group II: 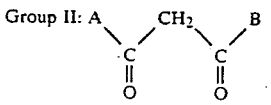 (5)

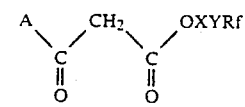 (6)

Group III: $HXY(Rf)_m$ (7)
$HVW(R^2)_b$ (8)

wherein m and b represent an integer of 1 or 2; X and V represent:

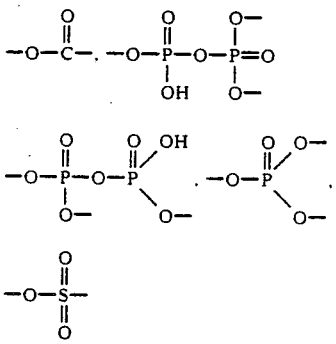

or $-O-$; Y and W represent $-C_kH_{2k}-$, $-(C_kH_{2k}O)_g-$ or a covalent bond (in which k represents an integer of 1 to 30, and g represents an integer of 1 to 10); $R^1$ and $R^2$ represent an alkyl group containing 1 to 30 carbon atoms; Rf represents $C_qF_{2q+1}$ or $C_qF_{2q}H$; and A and B represent $C_qH_{2p+1}$ or $C_JH_{2J+1}$ (in which p, q and J represent an integer of 1 to 30).

The SP value, which is an index of affinity for resins of the fluorinated carbon chain-containing aluminum compounds according to the invention can be varied by changing x and y in the above production processes, i.e., by changing the ratio of hydrocarbon chains to fluorinated carbon chains present around aluminum.

As examples of aluminum compounds usable as a starting material of Group I, mention may be made of trimethoxyaluminum, triethoxyaluminum, triisopropoxyaluminum and tributoxyaluminum. Triisopropoxyaluminum and tributoxyaluminum are preferable in respect of reactivity and cost. As examples of Rf contained in the starting materials represented by General Formulas (6) and (7), mention may be made of $CF_3$, $C_2F_5$, $C_3F_7$, $C_4F_9$, $C_5F_{11}$, $C_6F_{13}$, $C_7F_{15}$, $C_8F_{17}$, $C_{10}F_{21}$, $C_{10}F_{20}H$, $C_{11}F_{23}$, $C_{11}F_{22}H$, $C_{12}F_{25}$, $C_{12}F_{24}H$, $C_{13}F_{27}$, $C_{13}F_{26}H$, $C_{14}F_{29}$, $C_{14}F_{28}H$, $C_{15}F_{31}$, $C_{15}F_{30}H$, $C_{16}F_{33}$, $C_{16}F_{32}H$, $C_{17}F_{35}$, $C_{18}F_{37}$, $C_{18}F_{36}H$, and the like. Of these groups, $C_7F_{15}$, $C_7F_{14}H$, $C_8F_{17}$, $C_8F_{16}H$, $C_9F_{19}$, $C_9F_{18}H$, $C_{10}F_{21}$ and $C_{10}F_{20}H$ are preferable in respect of effects and cost.

As examples of spacers represented by Y or W which may be present in starting materials, mention be made of $CH_2$, $C_2H_4$, $C_3H_6$, $C_4H_8$, $C_5H_{10}C_6H_{12}$, $C_7H_{14}$, $C_8H_{16}$, $C_9H_{18}$, $C_{10}H_{20}$, and the like. Of these groups, $C_2H_4$, $C_4H_8$ and $C_6H_{12}$ are preferable.

As examples of R which may be contained in the starting material represented by General Formula (8), mention may be made of $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, $C_{11}H_{23}$, $C_{12}H_{25}$, $C_{13}H_{27}$, $C_{14}H_{29}$, $C_{15}H_{31}$, $C_{16}H_{33}$, $C_{17}H_{35}$, $C_{18}H_{37}$, $C_{19}H_{39}$, $C_{20}H_{41}$, and the like. Of these groups, $C_4H_9$, $C_6H_{13}$, $C_8H_{17}$, $C_{12}H_{25}$ and $C_{18}H_{37}$ are preferable.

As examples of starting materials represented by General Formula (5), mention may be made of acetylacetone, esters of acetoacetic acid, diesters of malonic acid, acetoacetic acid anilides, and the like. In cases where a compound (e.g., carboxylic acid) capable of ligation to a metal is used as a starting material, undesirable gelation may result due to intermolecular ligation of the compound. It is therefore necessary to use a raw material capable only of intramolecular ligation (e.g., dicarbonyl compound), so as to avoid gelation. Among compounds that form intramolecular ligation with aluminum, those capable of forming a 5- or 6-membered ring, in particular, those having no functional group which may form extramolecular ligation, are preferable. Because of this, ethyl acetoacetate and acetylacetone are preferable. The use of these compounds can also be advantageous in respect of cost and properties of products obtainable therefrom.

Fluorinated carbon chain-containing aluminum compounds according to the invention can be produced in accordance with the following procedure: An alkoxyaluminum compound selected from Group I is reacted with a fluorinated carbon chain-containing compound represented by General Formula (7) and a hydrocarbon chain-containing compound represented by General Formula (8), thereby using said fluorinated carbon chain-containing compound in an amount of x mol and said hydrocarbon chain-containing compound in an amount of y mol, per mol of said alkoxyaluminum compound (wherein x and y are numerals that satisfy: $0.1 \leq x \leq 2.5$, $0 \leq y \leq 2.5$ and $x+y \leq 2.5$); an alkoxyaluminum compound represented by Group I is reacted with a dicarbonyl compound represented by General Formula (5) and a fluorinated carbon chain-containing compound represented by General Formula (7), thereby using said dicarbonyl compound in an amount of x mol and said fluorinated carbon chain-containing compound in an amount of y mol, per mol of said alkoxyaluminum compound (wherein x and y are numerals that satisfy: $0.1 \leq x \leq 2.5$, $0.1 \leq y \leq 2.5$ and $0.1 \leq x+y \leq 2.5$); or an alkoxyaluminum compound selected from Group I is reacted with a dicarbonyl compound represented by General Formula (6) and a compound represented by General Formula (7) or (8) of Group III, thereby using said alkoxyaluminum compound in an amount of x mol and said Group III compound in an amount of y mol, per mol of said alkoxyaluminum compound (wherein x and y are numerals that satisfy: $0.1 \leq x \leq 2.5$, $0 \leq y \leq 2.5$ and $0.1 \leq x+y \leq 2.5$). The reaction is allowed to proceed for a few hours at ordinary temperature or at a temperature not higher than 100° C., without using any solvents or in an appropriate reaction medium, such as isopropyl alcohol, toluene and xylene. Then the alcohols formed and the solvents used, if any, are removed by means of distillation, to give the desired aluminum compound in the form of a highly viscous liquid, wax or powder. In cases where x or y is less than 0.1, a product will result which is no better than prior art aluminum couplers. In cases where $x+y \leq 2.5$, a product will result having only a poor reactivity. The isolated product obtained above can be used as a surface modifier for inorganic materials. The reaction mixture containing alcohols and solvents, if any, can also be used as a surface modifier.

The degree of oil repellency of the product can be varied by changing the molar ratio and the value of x and y. It is also possible to use the surface modifier of the present invention in combination with known surface modifiers. The amount of the present surface modifier to be used will vary depending, for example, on the kind of inorganic material to be treated, its specific surface area, and the amount of water bound to it. In cases where an inorganic filler is to be treated with a surface modifier according to the invention, it may be used in an amount of 0.05 to 20% by weight, preferably 0.2 to 10% by weight, based on the weight of the filler. In this case, the surface treatment of the filler can be effected, e.g., by: (1) a method in which the mixture is subjected to copolymerization, using a pulverizer, such as a Henschal mixer, a ball mill and an atomizer colloid mill; (2) a method wherein the modifier and the filler are added to an appropriate organic solvent, and then the mixture is stirred and admixed, followed by the removal of the solvent; and (3) a method where the modifier is directly added to a mixture of an organic medium and the filler, and the mixture is subjected to a mixing treatment, using heat rolls, for example.

In cases where the surface modifier according to the invention is used as a primer upon formation of a coated fluororesin or upon coating of a fluorine paint, the modifier per se can be coated on the surface of an organic material. Alternatively, the material can be treated with a solution of the modifier in an appropriate solvent, for example, toluene, xylene, benzene, hexane, cyclohexane, methylethyl ketone, acetone, acetonitrile, carbon tetrachloride, chloroform, methylenechloride, trichloroethylene, diethyl ether, tetrahydrofuran, or the like. Where required, the coated primer or primer solution is then dried at a temperature of 0° to 100° C.

As examples of inorganic materials to which the modifier of the invention can be applied, mention may be made of metals, such as iron, zinc, copper, nickel, tungsten, molybdenum, rhenium, niobium, tantalum lead, etc., metal oxides, such as tungsten trioxide, aluminum oxide, lanthanum oxide, cadmium oxide, chromium oxide, yttrium oxide, titanium oxide,, copper oxide, cuprous oxide, lead suboxide, zinc oxide, gadolinium oxide, iron susquioxide, tri-iron tetroxide, gamma-ferric oxide, ferrite, etc., metal carbonates, such as lead carbonate, strontium carbonate, calcium carbonate, barium carbonate, etc., hydroxides, such as aluminum hydroxide, magnesium hydroxide, chromium hydroxide, nickel hydroxide, etc., pigments, such as chromium lead, prussian blue, ultramarine, cobalt blue, chromium phosphate, zinc phosphate, lead cyanamide, calcium plumbate, basic silicochromates, carbon pigments, chrome yellow, cadmium yellow, zinc yellow, naples yellow, rhodamine, Benzidine yellow, etc., talc, kaolin, silica, bentonite, glass, tungsten carbide, ammonium paratungstate, glass wool, silicon carbide, acetylene black, graphite, carbon black, barium titanate, cadmium sulfide, barium sulfate, carbon fluoride, graphite fluoride, granular ammonium chloride, litharge, titanozirconates, ammonium dihydrogenphosphate, ethylenediamine tartrate, and the like.

It is also possible to apply the surface modifier of the invention to organic materials, including, e.g., organic pigments, such as Phthalocyanine Blue, Hansa yellow, Litol Red, Phthalocyanine Green, Quinacridone Red and Aniline Black. There is no restriction on the physical state of inorganic and organic materials to which the modifier is applied. Such materials can be in any state, including, e.g., powders, granules, bars, plates, lines, masses and wools.

Inorganic fillers treated with the surface modifier of the invention can be particularly advantageous when filled into a fluororesin. By the term "fluororesin" is herein meant a polymer produced from a monomer containing within the molecule at least one fluorine atom. As examples of such polymers, mention may be made of polymers of fluoroethylenes, such as $CF_2=CF_2$, $CHF=CF_2$, $CH_2=CF_2$, $CH_2=CHF$, $CClF=CF_2$, $CHCl=CF_2$, $CCl_2=CF_2$, $CClF=ClF$, $CHF=CCl_2$ $CH_2=CClF$, $CCl_2=CClF$, etc., fluoropropenes, such as $CF_3CF=CF_2$, $CF_3CF=CHF$, $CF_3CH=CF_2$, $CF_3CF=CH_2$, $CH_3CF=CHF$, $CHF_2CF=CHF$, $CF_3CH=CH_2$, $CH_3CF=CF_2$, $CH_3CH=CF_2$, $CH_3CF=CH_2$, $CF_2ClCF=CF_2$, $CF_3CCl=CF_2$, $CF_3CF=CFCl$, $CF_2ClCCl=CF_2$, $CF_2ClCF=CFCl$, $CFCl_2CF=CF_2$, $CF_3CCl=CClF$, $CF_3CCl=CCl_2$, $CClF_2CF=CCl_2$, $CCl_3CF=CF_2$, $CF_2ClCCl=CCl_2$, $CFCl_2CCl=CCl_2$, $CF_3CF=CHCl$, $CClF_2CF=CHCl$, $CF_3CCl=CHCl$, $CHFCCl=CCl_2$, $CF_2ClCH=CCl_2$, $CF_2ClCCl=CHCl$, $CCl_3CF=CHCl$, $CF_2ICF=CF_2$, $CF_2BrCH=CF_2$, $CF_3CBr=CHBr$, $CF_2ClCBr=CH_2$, $CH_2BrCF=CCl_2$, $CF_3CBr=CH_2$, $CF_2CH=CHBr$, $CF_2BrCH=CHF$, $CF_2BrCF=CCl_2$, etc., fluoroolefins containing 4 or more carbon atoms, such as $CF_3CF_2CF=CF_2$, $CF_3CF=CFCF_3$, $CF_3CH=CFCF_3$, $CF_2=CFCF_2CHF_3$, $CF_3CF=CFCF_3$, $CF_3CH=CFCF_3$, $CF_2CF=CFCF_2CHF_3$, $CF_3CF_2CF=CH_2$, $CF_3CH=CHCF_3$, $CF_2CFCF_2CH_3$, $CF_2=CFCH_2CH_3$, $CF_3CH_2CH=CH_2$, $CF_3CH=CHCH_3$, $CF_2CH=CH_2CH_3$, $CH_3CF_2CH=CH_2$, $CFH_2CH=CHCFCH_2$, $CH_3CF_2CH=CH_3$, $CH_2=CFCH_2CH_3$, $CF_3(CF_2)2CF=CF_2$, $CF_3(CF_2)3CF$ etc., and perfluoroalkyl vinyl ethers, such as $CF_2=CF-OC_3F_7$, etc.; copolymers of two or more of these monomers; and copolymers produced from these monomers and other polymerizable monomers, such as ethylene, propylene, 1-butene, vinyl chloride, vinyl ethers, (meth)acrylic acid, (meth)acrylates, etc. The surface modifier of the present invention can be applied as a primer to the surface of an inorganic material at the time when a film of a fluororesin is formed on the surface of the material or at the time when a paint containing a fluororesin is painted thereon, so as to improve the adhesion of the fluororesin or paint to the inorganic material. Inorganic materials treated with the surface modifier of the invention may also be filled into other resins, such as natural rubbers; synthetic rubbers, such as styrene-butadiene rubbers, urethane rubbers, etc.; polyolefin resins, such as polyethylenes, polypropylenes, etc.; polyacrylonitriles; polybutadienes; butadieneacrylonitrile copolymers; copolymers of ethylene and other copolymerizable monomers, such as propylene, 1-butene, vinyl acetate and maleic anhydride; polycarbonate resins; phenoxy resins; polyvinyl chlorides; copolymers of vinyl chloride and vinyl acetate or other vinyl esters; polyvinyl acetates; polyvinyl acetals; polyvinylidene chlorides; vinylidene chloride-vinyl chloride-acrylic acid copolymers; epoxy resin; phenol resins; silicone resins; and polyester resins.

The present invention will be further illustrated by the following examples. It should however be understood that these examples are intended to clarify thd nature of the invention and are not to be construed to limit the scope of the invention.

EXAMPLE 1

Synthesis of isopropoxynonadecafluorodecanoylaluminum ethylacetoacetate

Figure 3:
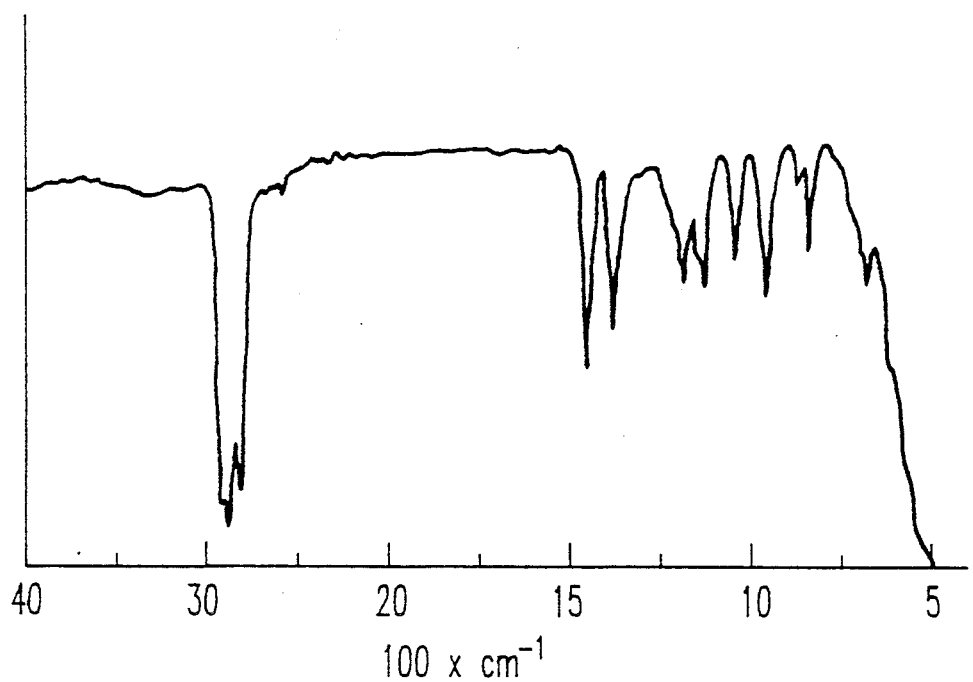
FIGS. 3, 6, 12 and 13 show infrared absorption spectra of starting compounds.
Figure 4:
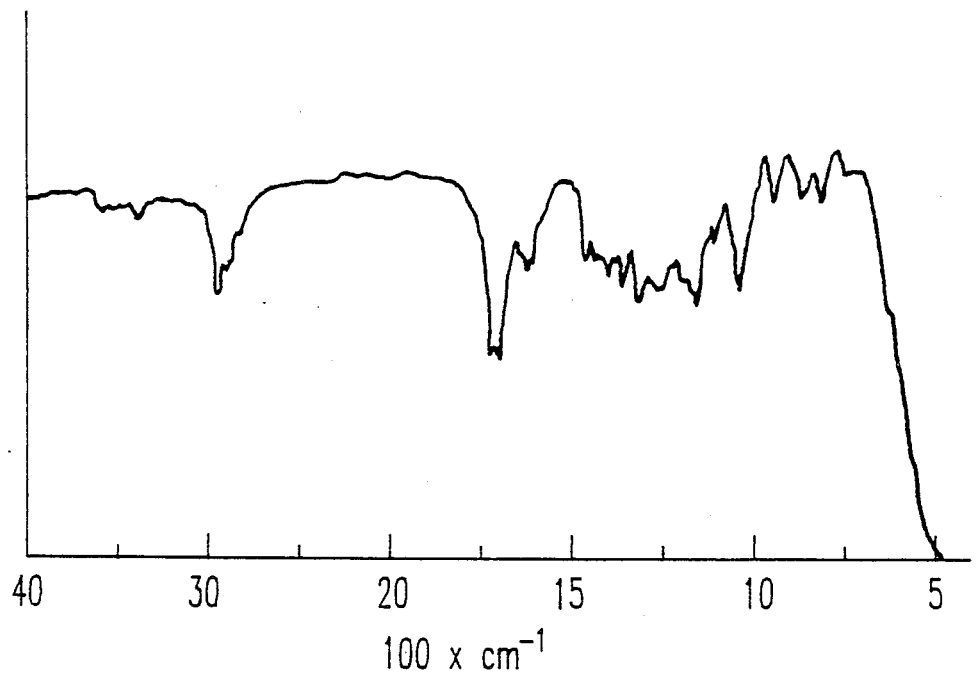
FIG. 4: Ethyl acetoacetate
Figure 6:
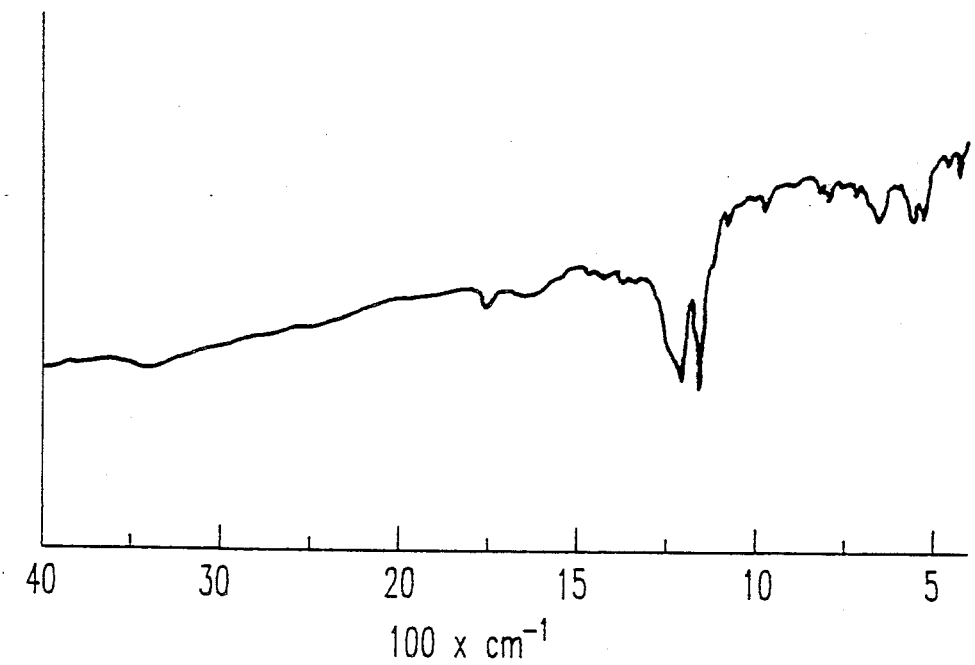
Figure 7:
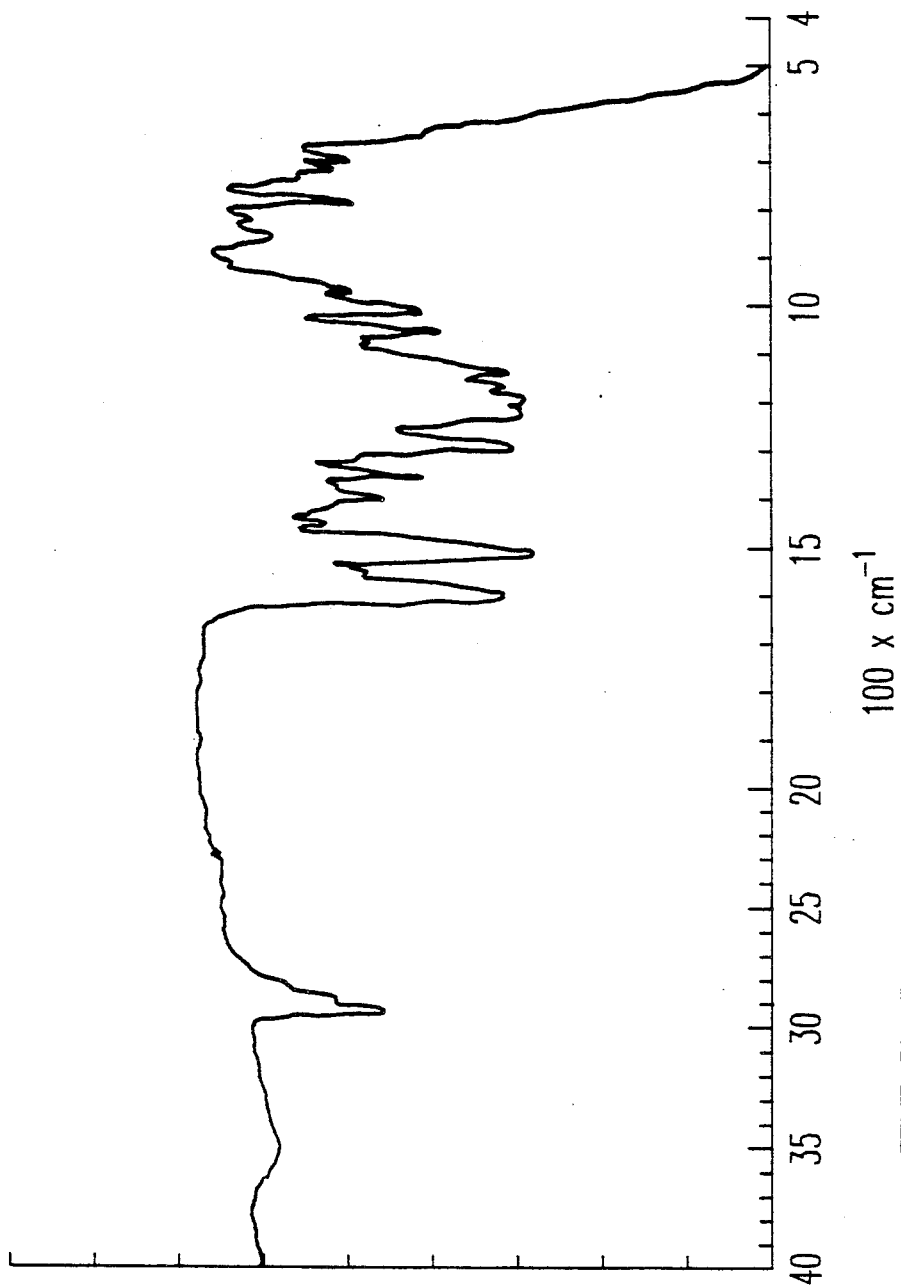
Figure 8:
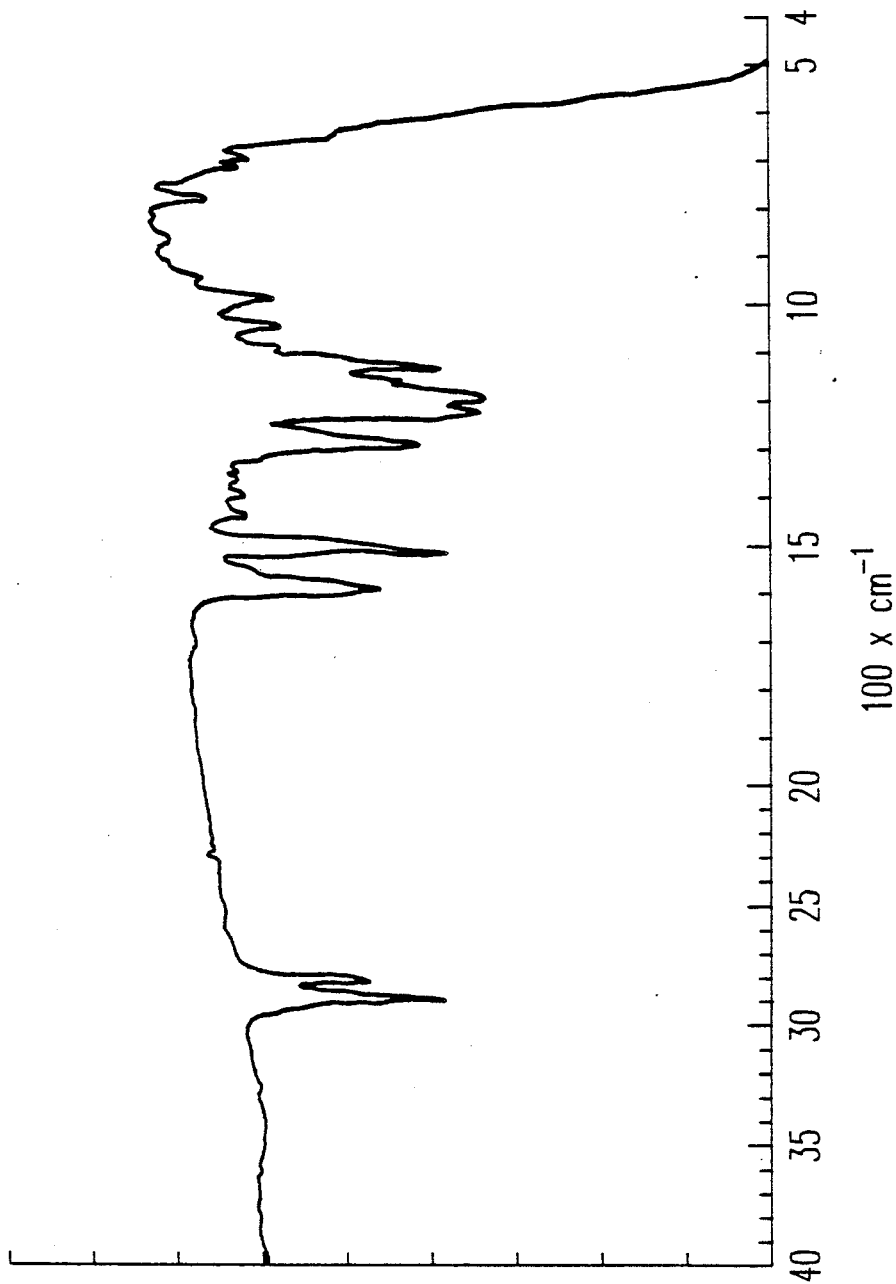
Figure 9:
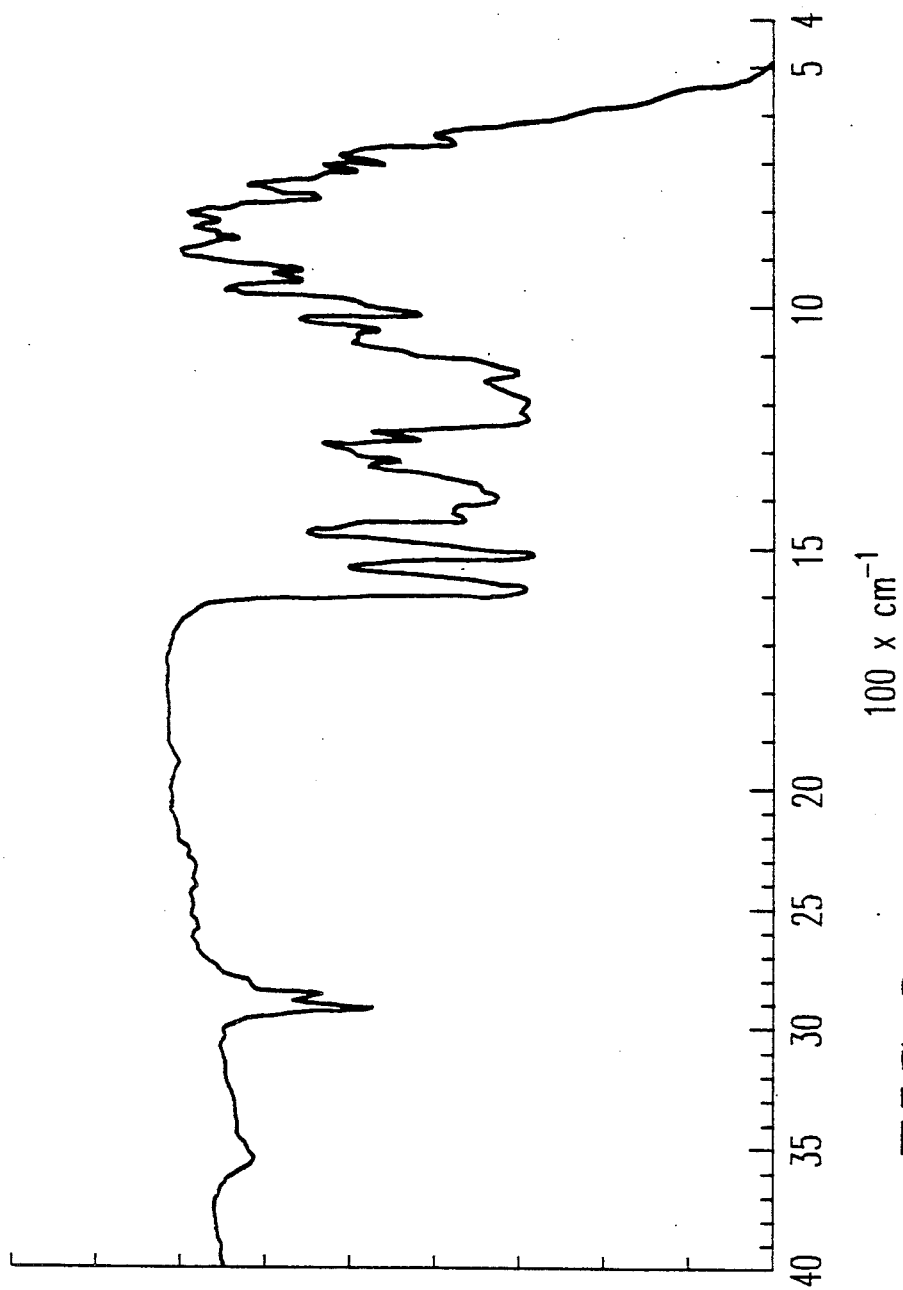
Figure 10:
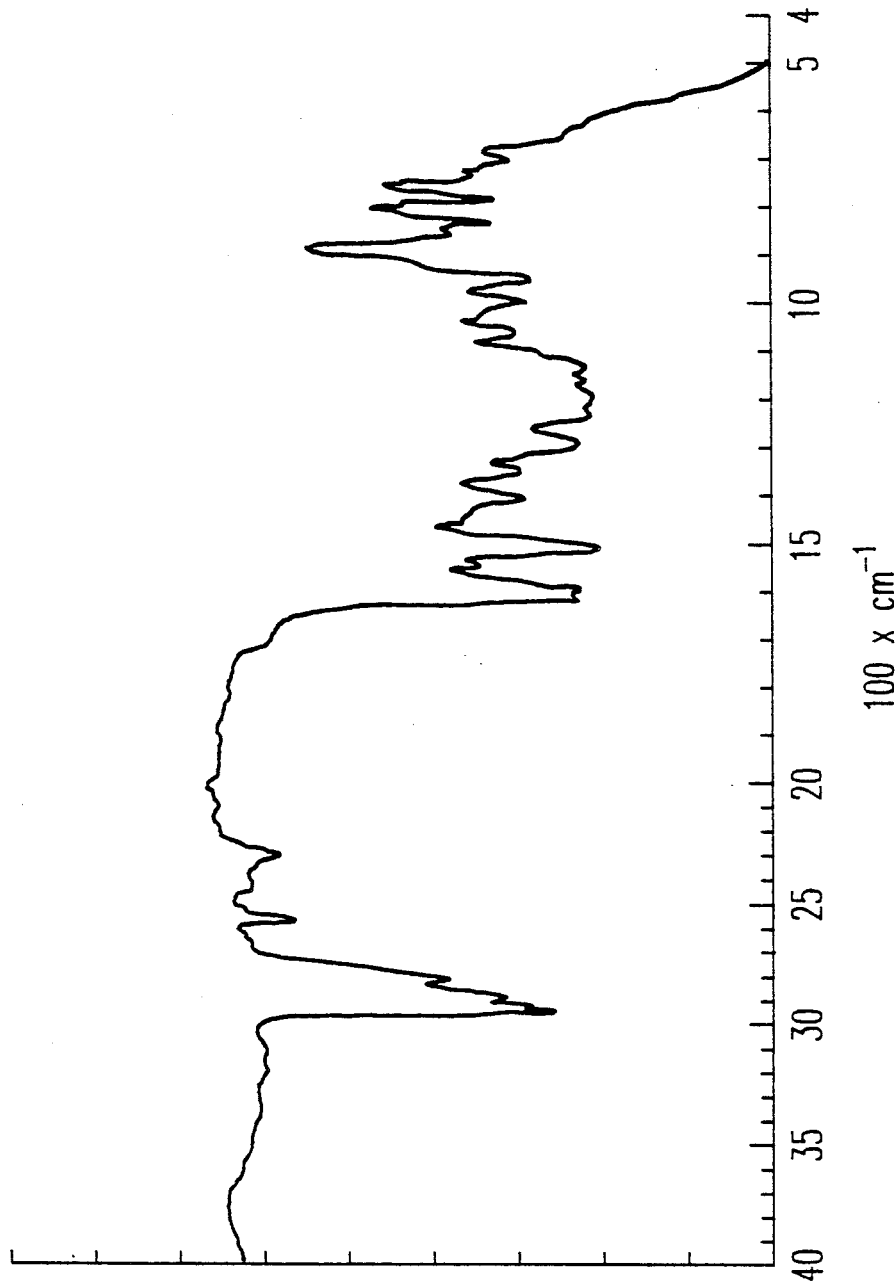
Figure 11:
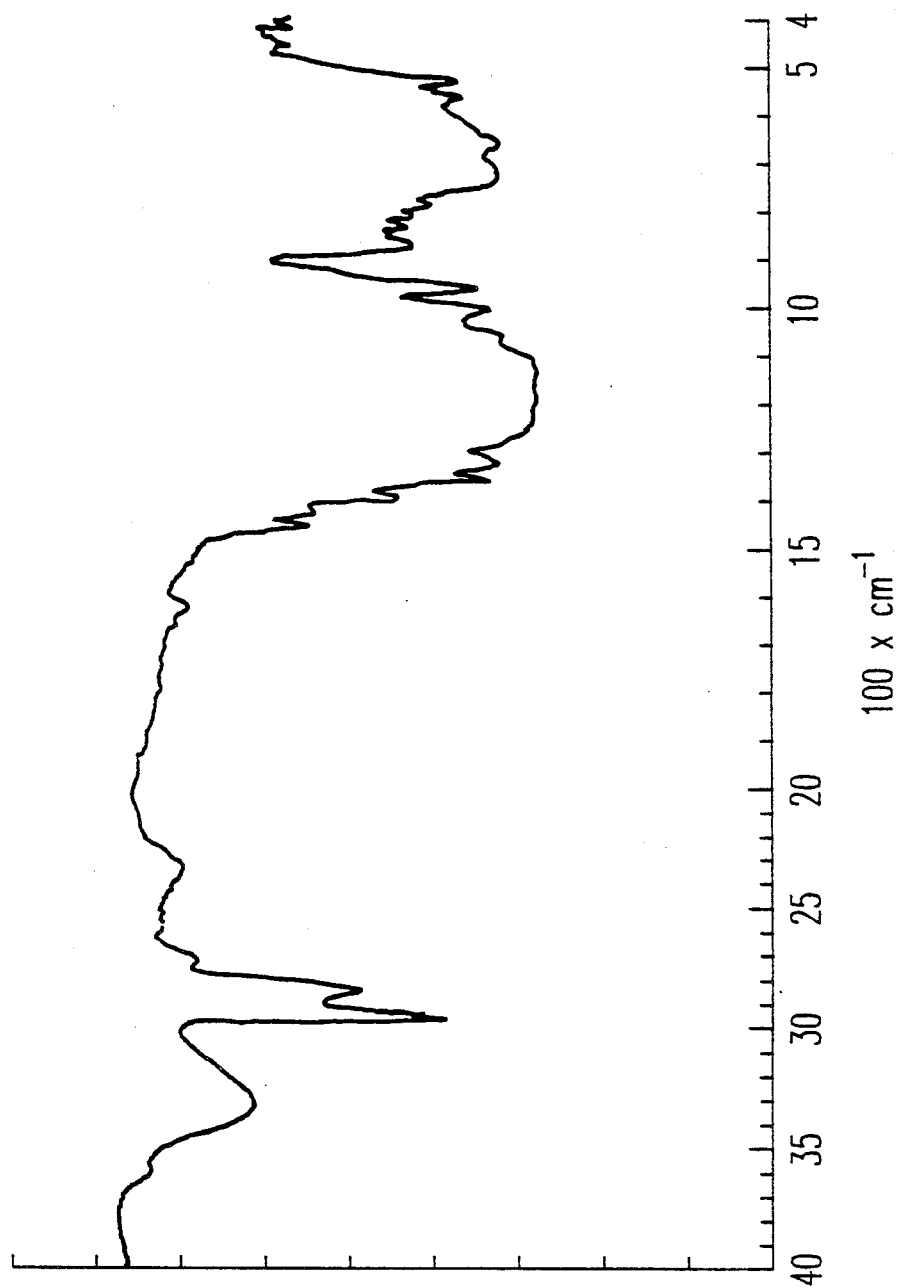
Figure 12:
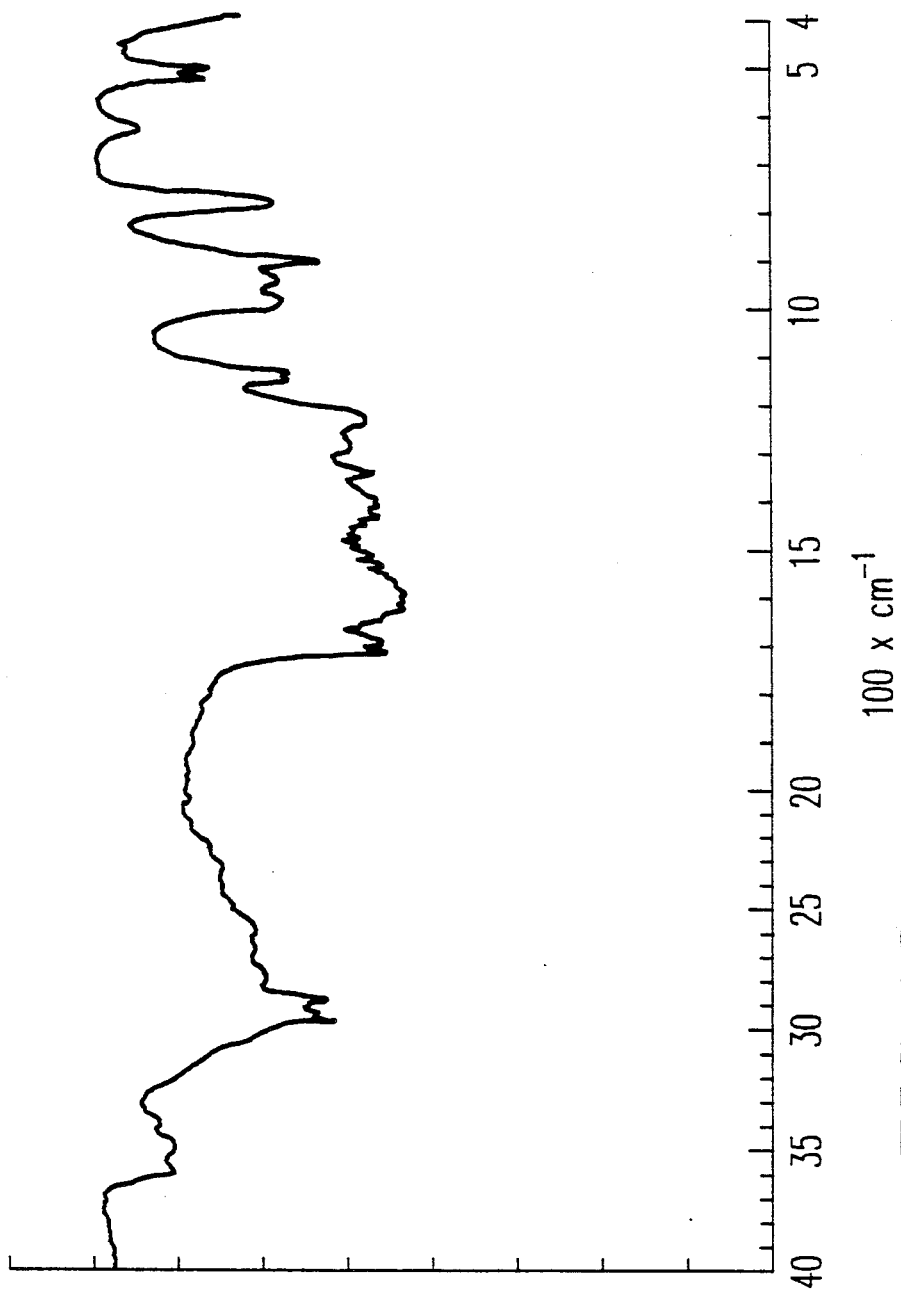
Figure 13:
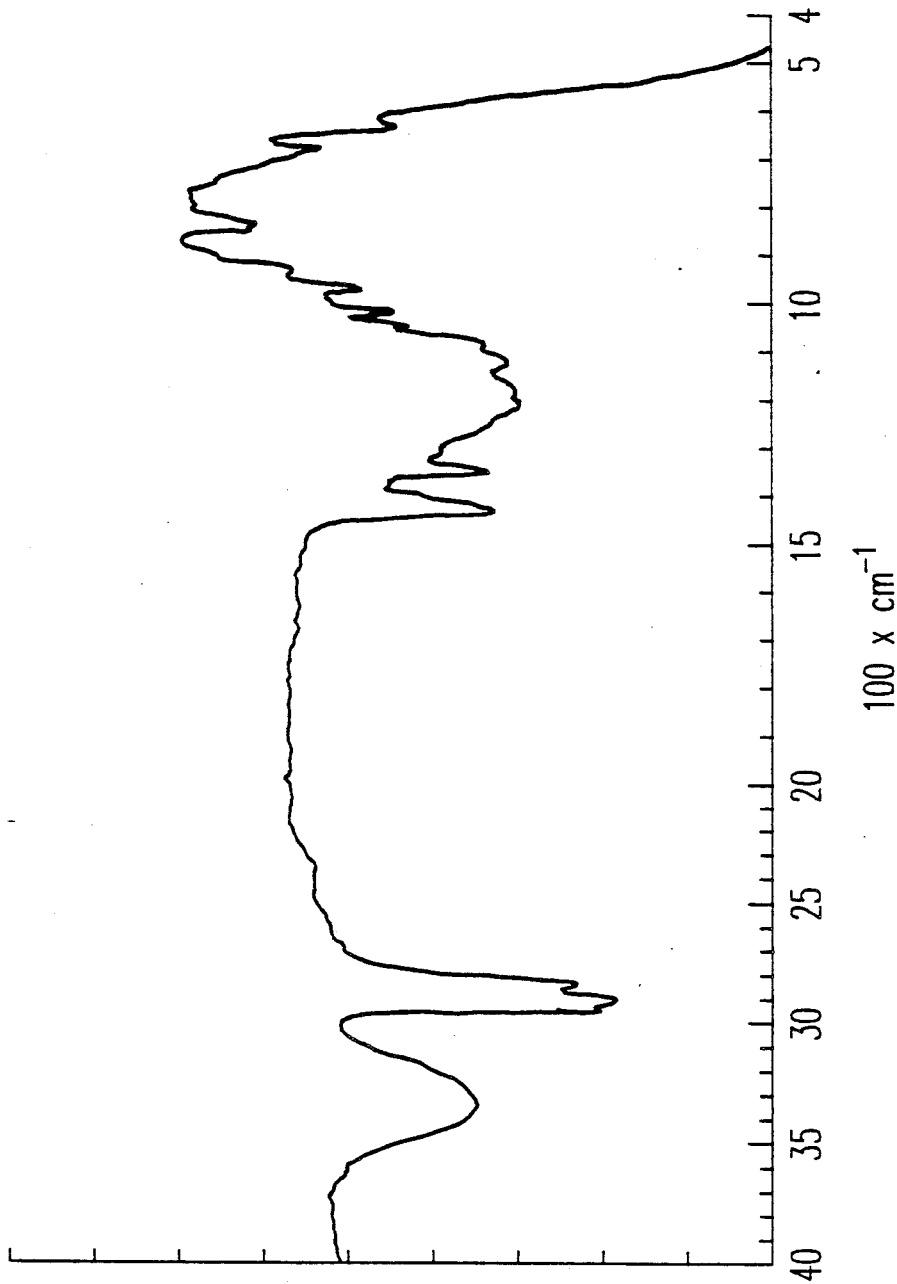

To 2.0 g (9.8 mmol) of aluminum triisopropoxide was gradually dropped with stirring at room temperature a solution of 1.28 g (9.8 mmol) of ethyl acetoacetate in toluene (2 ml), and the resulting mixture was stirred for 30 minutes at 60° C. Then, 9.1 g (0.018 mol) of nonadecafluorodecane was gradually added thereto, and the resulting mixture was stirred for 30 minutes at 50° C. After the mixture had been stirred for additional 1.5 hours at 60° C., isopropyl alcohol and toluene were distilled off under reduced pressure to give a viscous reddish-brown liquid. The IR spectrum of the product is shown in FIG. 1. The spectrum, which is different from those of the starting materials shown in FIGS. 3, 4 and 6, shows that a new product was obtained by the reaction.

EXAMPLE 2

Synthesis of isopropoxynonadecafluorodecanoylaluminum octadecylacetoacetate

Figure 2:
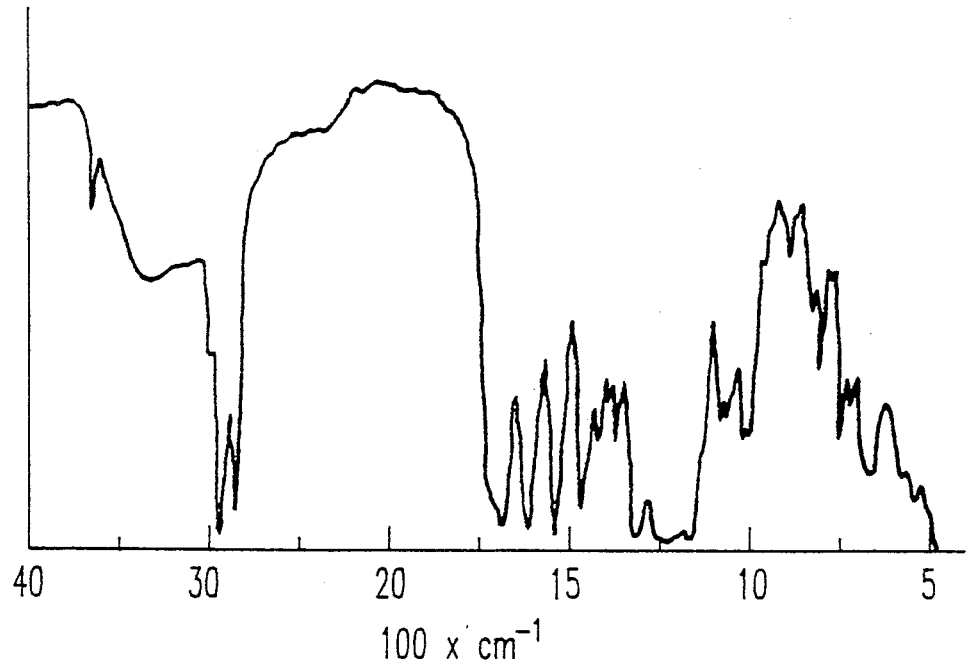
Figure 5:
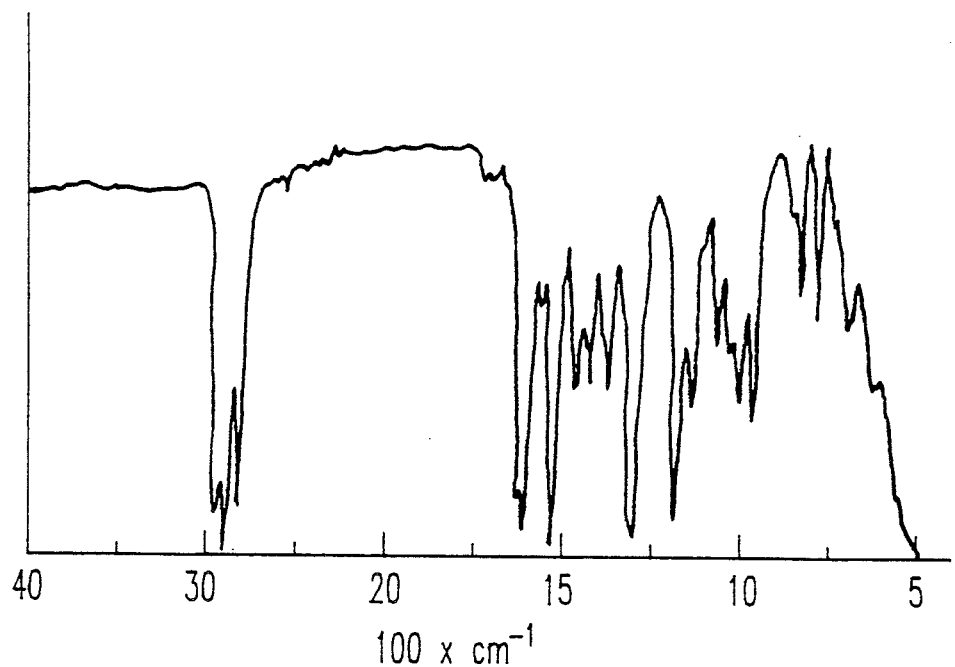
FIG. 5: AL-M

To a solution of 2.0 g of an aluminum coupler (AL-M manufactured by Ajinomoto Co., Inc.) in toluene (2 ml) was added with stirring at room temperature 2.9 g (5.64 mmol) of nonadecafluorodecanoic acid, and the resulting mixture was stirred at 50° C. for 30 minutes. After the mixture had been stirred at 60° C. for an additional 1 hour, toluene and isopropyl alcohol were distilled off to give an orange-colored creamy product. The IR spectrum of the product is shown in FIG. 2. The spectrum, which is different from those of the starting materials shown in FIGS. 5 and 6, shows that a new product was obtained by the reaction.

EXAMPLE 3

Synthesis of isopropoxynonadecafluorodecanoylaluminum octadecylacetoacetate (No solvent reaction)

To 2.0 g of aluminum coupler (AL-M manufactured by Ajinomoto Co., Inc.) was gradually added with stirring at room temperature 2.9 g (5.64 mmol) of nonadecafluorodecanoic acid, and the resulting mixture was stirred at 50° C. for 30 minutes. Then, the mixture was stirred at 60° C. for an additional 1 hour to give a viscous reddish-brown liquid.

EXAMPLE 4

Synthesis of isopropoxynonadecafluorodecanoylaluminum acetylacetonate

To 2.0 g (9.8 mmol) of aluminum triisopropoxide was gradually added with stirring at room temperature 1.0 g (9.98 mmol) of acetylacetone, and the resulting mixture was stirred for 30 minutes at 60° C. To this was gradually added 5.13 g (10.0 mmol) of nonadecafluorodecanoic acid, and the resulting mixture was stirred it 50° C. for 30 minutes. After the mixture had been stirred at 60° C. for an additional 1 hour, isopropyl alcohol and toluene were distilled off under reduced pressure to give a viscous reddish-browns liquid. When this reaction was repeated without using any solvents, it was impossible to continue the stirring until the end of the reaction.

EXAMPLE 5

To 20 g of titanium dioxide was added 0.2 g (1.0 %) of the surface modifier prepared in Example 1, and the mixture was subjected to dry blending for 3 minutes by using a coffee mill. A test piece was prepared by pressing the powders with an IR tablet machine at a pressure of 100 kg/cm$^2$ for 3 minutes. A drop of water was dropped on the test piece, and the contact angle between them was measured immediately after the dropping, using an automatic angle measuring apparatus (Table 1). Oil absorption of the powders was then determined as follows: 2.0 g of powders prepared above was placed on a glass plate and then kneaded with a metal knife, during which paraffin was gradually added thereto until the mixture was turned into a putty-like state, which was regarded to be the end point of its oil absorption (Table 1).

EXAMPLE 6

The procedure of Example 5 was repeated by using 20 g of titanium dioxide and 0.2 g (1.0%) of the surface modifier prepared in Example 3, and the contact angle of the tablet and the oil absorption of the powders treated with the modifier were determined in the same manner (Table 1).

EXAMPLE 7

The procedure of Example 5 was repeated by using 20 g of titanium dioxide and 0.2 g (1.0 %) of the surface modifier prepared in Example 4 and the contact angle of the tablet and the oil absorption of the powders treated with the modifier were determined in the same manner (Table 1).

COMPARATIVE EXAMPLE 1

The procedure of Example 5 was repeated by using 20 g of titanium dioxide and 0.2 g (1.0 %) of AL-M, and the contact angle of the tablet and the oil absorption of the powders treated with the modifier were determined in the same manner (Table 1).

EXAMPLE 8

Into 10 ml of tetrahydrofuran was dissolved 0.1 g of the surface modifier prepared in Example 1. A cover glass was dipped in the resulting solution for 10 minutes and then air dried. On the surface of the thus treated cover glass was dropped liquid paraffin, and the contact angle between them was determined immediately after the dropping (Table 2).

EXAMPLE 9

The surface of a cover glass was treated in the same manner as in Example 8, using the surface modifier prepared in Example 3, and then the contact angle it formed between the glass and liquid paraffin was determined (Table 2).

EXAMPLE 10

The surface of a cover glass was treated in the same manner as in Example 8, using the surface modifier prepared in Example 4, and then the contact angle formed between the glass and liquid paraffin was determined (Table 2).

COMPARATIVE EXAMPLE 2

The surface of a cover glass was treated with AL-M in the same manner As in Example 10, and the contact angle between the glass and liquid paraffin was determined (Table 2).

EXAMPLE 11

Into a solution in toluene (10 ml) of 0.1 g of the surface modifier prepared in Example 1 was dispersed 10 g of carbon black (FW-200 manufactured by Degussa), and then the solvent was distilled off under reduced pressure. The dispersibility of the thus treated carbon black into a fluororesin was then examined in the following manner.

The following components:

| | |
|---|---|
| KF polymer U-1000 (by Kureha Chemical Ind.) | 5 parts |
| The surface treated carbon black | X parts |
| DMF | (5 + X) parts |

(wherein X = 1, 3 or 5)

were heated and stirred in a container to form a dispersion. After being cooled to room temperature, the dispersion was coated on a separating paper at a thickness of 0.25 mm and then heated in a gear oven at 120° C. for 5 minutes, to form a black resin film. The carbon black, which was treated with a surface modifier according to the invention, was well dispersed in the KF polymer, and the surface of the resin was smooth.

EXAMPLE 12

A resin film was prepared in the same manner as in Example 11, except that the surface modifier obtained in Example 3 was used. The carbon black was well dispersed in the resin film, and the surface of the film was smooth.

EXAMPLE 13

A resin film was prepared in the same manner as in Example 11, except that the surface modifier prepared in Example 4 was used. The carbon black was well dispersed, and the surface of the resin film was smooth.

COMPARATIVE EXAMPLE 3

A resin film was prepared in the same manner as in Example 13, except that AL-3 was used as surface modifier. The dispersibility of carbon black was poor and the surface of the film was rough, in comparison with Example 13.

TABLE 1

Contact Angle and Oil Absorbance of Surface-treated Titanium Dioxide

| | Contact Angle | Oil Absorbance |
|---|---|---|
| Example 5 | 123.5° | 25 g/100 g |
| Example 6 | 130.0° | 26 g/100 g |
| Example 7 | 124.3° | 20 g/100 g |
| Comparative Example 1 | 111.0° | 25 g/100 g |

TABLE 2

Contact Angle between Liquid Paraffin and Surface-treated Cover Glass

| | Contact Angle |
|---|---|
| Example 8 | 70° |
| Example 9 | 62° |
| Example 10 | 70° |

TABLE 2-continued

| Contact Angle between Liquid Paraffin and Surface-treated Cover Glass | |
|---|---|
| | Contact Angle |
| Comparative Example 2 | 10° |
| Non-treated Glass | 20° |

EXAMPLE 14

Synthesis of isopropoxy 1H,1H,2H,2H-perfluorodecanoxyaluminum ethylacetoacetate

To 38.4 g (0.29 mol) of ethyl acetoacetate was gradually dropped with stirring at room temperature a solution of 60 g (0.29 mol) of aluminum triisopropoxide in 50 ml of isopropyl alcohol, and the resulting mixture was stirred for 2 hours at 60° C. To this was gradually added 136.5 g (0.29 mol) of 1H,1H,2H,2H-perfluorodecanol, and the reaction was allowed to proceed for 1 hour at reflux temperature. Thereafter, isopropoxy alcohol was distilled off under reduced pressure to give a viscous colorless liquid. The IR spectrum of the product showed that a new product different from the starting materials was obtained.

EXAMPLE 15

Synthesis of isopropoxy 1H,1H,2H,2H-perfluorodecanoxyaluminum octadecylacetoacetate To 96 g of an aluminum coupler (AL-M manufactured by Ajinomoto Co.) was added with stirring at room temperature 89.3 g (0.019 mol) of 1H,1H,2H,2H-perfluorodecanol. The resulting mixture was stirred at 50° C. for 30 minutes, and then the reaction was allowed to proceed at reflux temperature for 1 hour. Thereafter, isopropyl alcohol formed as by-product was distilled off to obtain a viscous yellow liquid. The IR spectrum of the product showed that a new product different from the starting materials was obtained.

EXAMPLE 16

Synthesis of isopropoxy 1H,1H,2H,2H-perfluorodecanoxyaluminum acetylacetonate

To a solution of 1 g (4.9 mmol) of aluminum triisopropoxide in 5 ml of isopropyl alcohol was gradually dropped with stirring at room temperature 0.5 g (4.9 mmol) of acetylacetone, and the resulting mixture was stirred for 2 hours at 60° C. Then, 2.27 g (4.9 mmol) of 1H,1H,2H,2H-perfluorodecanol was gradually added thereto, and the reaction was allowed to proceed for 1 hour at reflux temperature. Thereafter, isopropyl alcohol was distilled off under reduced pressure to give a viscous light yellow liquid. The IR spectrum of the product showed that a new product different from the starting materials was obtained.

EXAMPLE 17

Synthesis of diisopropoxyaluminum 1H,1H,2H,2H-perfluorodecylacetoacetate

To a mixture of 35.7 g (76.9 mmol) of 1H,1H,2H,2H-perfluorodecanol and 0.2 g (0.7 mmol) of tetraisopropyl titanate was dropped with stirring at 40° to 50° C. ethyl acetoacetate and, while removing ethanol formed as byproduct, the resulting mixture was stirred for 2 hours, during which its temperature was raised up to 100° C. The yellow liquid obtained was distilled under reduced pressure to give a distillate (110° to 118° C.), which was identified is 1H,1H,2H,2H-perfluorodecyl acetoacetate, by means of IR, proton NMR and MS. To 1 g of triisopropoxy aluminum was added 2.69 g (4.9 mmol) of the acetoacetate and, while removing isopropanol formed as by-product, the resulting mixture was stirred at 120° C. for 2 hours to give a viscous light yellow liquid. The IR spectrum of the product showed that a new product different from the starting materials was obtained.

EXAMPLE 18

Synthesis of isopropoxy di-1H,1H,2H,2H-perfluoro decanoxyaluminum

To a solution of 1 g of triisopropoxy aluminum in 4 ml of toluene was added 4.55 g (9.8 mmol) of 1H,1H,2H,2H-perfluorodecanol. While removing isopropanol formed as by-product, the reaction mixture was heated with stirring at reflux temperature for a period of 1 hour, to give a viscous colorless liquid. The IR spectrum of the product showed that a new product different from the starting materials was obtained.

EXAMPLE 19

To 10 g of titanium dioxide was added 0.1 g of the surface modifier prepared in Example 14, and the resulting mixture was admixed in a coffee mill. The thus created powders were shaped into tablets by using an IR tablet machine one drop of water or liquid paraffin was dropped onto a tablet, and the contact angle between them was determined immediately after the dropping (Table 3).

EXAMPLE 20

The procedure of Example 19 was repeated, except that titanium dioxide was treated with the surface modifier prepared in Example 15, and the contact angle between the tablet and water or liquid paraffine was determined (Table 3).

EXAMPLE 21

The procedure of Example 19 was repeated, except that titanium dioxide was treated with the surface modifier prepared in Example 16, and the contact angle between the tablet and water or liquid paraffin was determined (Table 3).

EXAMPLE 22

The procedure of Example 19 was repeated, except that titanium dioxide was treated with the surface modifier prepared in Example 17, and the contact angle between the tablet and water or liquid paraffin was determined (Table 3).

EXAMPLE 23

The procedure of Example 19 was repeated, except that titanium dioxide was treated with the surface modifier prepared in Example 18, and the contact angle between the tablet and water or liquid paraffine was determined (Table 3).

COMPARATIVE EXAMPLE 4

Titanium dioxide treated with AL-M in the same manner as in Example 19, and the contact angle of the tablet with water or liquid paraffine was determined (Table 3).

COMPARATIVE EXAMPLE 5

Titanium dioxide was treated with a titanate coupler (PLENACT TTS manufactured by Ajinomoto Co.), and the contact angle between the table and the water or liquid paraffin was determined (Table 3).

TABLE 3

| Contact Angle Formed between Surface-treated Titanium Dioxide and Water or Liquid Paraffin | | |
|---|---|---|
| | Water | Liquid Paraffin |
| Example 19 | 23.0° | 40.2° |
| Example 20 | 117.1° | 34.1° |
| Example 21 | 46.5° | 45.6° |
| Example 22 | 135.5° | 109.5° |
| Example 23 | 123.8° | 105.1° |
| Comparative Example 4 | 111.0° | 18.4° |
| Comparative Example 5 | 132.0° | 21.2° |

The surface modifier of the invention imparts excellent water- and oil-repelling, properties to inorganic materials, and inorganic materials treated with the modifier exhibit excellent affinity to, and dispersibility in, organic media, in particular, fluororesins and fluorine-containing paints. Numerous modifications of the present invention are possible in light of the above teachings. It is therefore to be understood that within the scope of the appended claims, the invention may be practiced other wise than as specifically described herein.

What is claimed as new and desired to be secured by letters patent of the United States is:

1. A fluorine-containing surface modifier comprising at least one member selected from the group consisting of: fluorinated carbon chain-containing aluminum compounds represented by the following formulae (1), (2) or (3):

$$(R^1O)_n Al[XY(Rf)_m]_L[VW(R^2)_b]_{3-n-L} \quad (1)$$

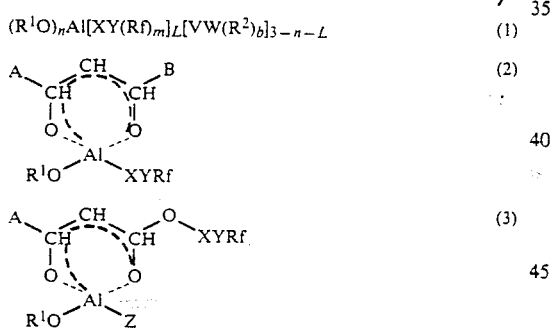

wherein n, m, L and b represent an integer of 1 or 2 (n and L satisfy: n+L<3); X and V represent $$-O-\overset{\overset{\displaystyle O}{\|}}{\underset{\underset{\displaystyle O}{\|}}{S}}-$$

—O—; Y and W represent —$C_kH_{2k}$—, —($C_kH_{2k}O$)— or a covalent bond (in which k represents an integer of 1 to 30, and g represents an integer of 1 to 10); $R^1$ and $R^2$ represents an alkyl group containing 1 to 30 carbon atoms; Rf represents $C_qF_{2q+1}$ or $C_qF_{2q}H$; A and B represent $C_pH_{2p+1}$ or $C_JH_{2J+1}O$ (in which p, q and J represent an integer of 1 to 30); and Z represents $VR^2$ or VWRF.

2. Fluorinated carbon chain-containing aluminum compounds obtained by:

alkoxy exchange reaction of an alkoxy aluminum compound selected from Group I set forth below with a fluorinated carbon chain-containing compound represented by formula (7) set forth below and a hydrocarbon chain-containing compound represented by formula (8) set forth below, in which said fluorinated carbon chain-containing compound is used in an amount of x mol and said hydrocarbon chain-containing compound in an amount of y mol, per mol of said alkoxy aluminum compound, wherein x and y are numerals that satisfy: $0.1 \leq x \leq 2.5$, $0.1 \leq y \leq 2.5$ and $0.1 \leq x+y \leq 2.5$; or alkoxy exchange reaction of an alkoxy aluminum compound selected from Group I set forth below with a dicarbonyl compound represented by formula (5) set forth below and a fluorinated carbon chain-containing compound represented by formula (7) set forth below, in which said fluorinated carbon chain-containing compound is used in an amount of x mol and said hydrocarbon chain-containing compound in an amount of y mol, per mol of said alkoxy aluminum compound (wherein x and y are numerals that satisfy: $0.1 \leq x \leq 2.5$, $0 \leq y \leq 2.5$ and $0.1 \leq x+y \leq 2.5$); or alkoxy exchange reaction of an alkoxy aluminum compound selected from Group I set forth below with a dicarbonyl compound represented by formula (6) set forth below and a compound represented by formula (7) or (8) of Group III set forth below, in which said dicarbonyl compound is used in an amount of x mol and said Group III compound in an amount of y mol, per mol of said alkoxy aluminum compound (wherein x an y are numerals that satisfy: $0.1 \leq x \leq 2.5$, $0 \leq y \leq 2.5$ and $0.1 \leq x+y \leq 2.5$)

Group I: $(R^1O)_3Al$     (4)

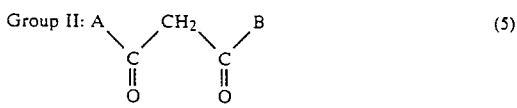

Group II: (5)

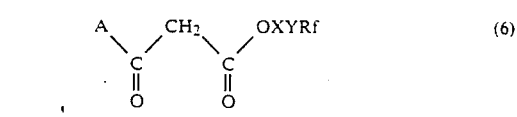

(6)

Group III: $HXY(Rf)_m$     (7)
$HVW(R^2)_b$     (8)

wherein m and b represent an integer of 1 or 2; X and V represent:

or —O—; Y and W represent —$C_kH_{2k}$—, —($C_kH_{2k}O$)$_g$— or a covalent bond (in which k represents an integer of 1 to 30, and g represents an integer of 1 to 10); $R^1$ and $R^2$ represent an alkyl group containing 1 to 30 carbon atoms; Rf represents $C_qF_{2q+1}$ or $C_qF_{2q}H$; and A and B represent $C_qH_{2p+1}$ or $C_JH_{2J+1}$ (in Which p, q and J represent an integer of 1 to 30).

3. A surface-modified filler comprising an effective amount of the fluorine-containing surface modifier of claim 1 and an organic or an inorganic filler.

4. The surface-modified filler of claim 3 comprising 0.05 to 20% by weight of fluorine-containing surface modifier.

* * * * *

UNITED STATES PATENT AND TRADEMARK OFFICE
CERTIFICATE OF CORRECTION

PATENT NO. : 5,142,079
DATED : AUGUST 25, 1992
INVENTOR(S) : NAOKI CHIBA ET AL

It is certified that error appears in the above-indentified patent and that said Letters Patent is hereby corrected as shown below:

Col. 13, line 51, Claim 1, "$-O-\overset{\overset{O}{\|}}{\underset{\underset{O}{\|}}{S}}-$" should read -- $-O-\overset{O}{\underset{}{\overset{\|}{C}}}-$  $-O-\overset{\overset{O}{\|}}{\underset{\underset{O}{\|}}{S}}-$ --

Col. 14, line 49, Claim 2, "$-O-\overset{\overset{O}{\|}}{\underset{\underset{O}{\|}}{S}}-$" should read -- $-O-\overset{O}{\underset{}{\overset{\|}{C}}}-$  $-O-\overset{\overset{O}{\|}}{\underset{\underset{O}{\|}}{S}}-$ --

Signed and Sealed this

Second Day of August, 1994

Attest:

BRUCE LEHMAN

*Attesting Officer*   *Commissioner of Patents and Trademarks*